US008368877B2

(12) United States Patent
Bataillou et al.

(10) Patent No.: US 8,368,877 B2
(45) Date of Patent: Feb. 5, 2013

(54) MEASURING APPARATUS

(75) Inventors: Benoit Bataillou, Lyons (FR); Pascal Bancken, Opwijk (BE); David van Steenwinckel, Holsbeek (BE); Viet Nguyen Hoang, Leuven (BE); Radu Surdeanu, Roosbeek (BE)

(73) Assignee: NXP B.V., Eindhoven (NL)

( * ) Notice: Subject to any disclaimer, the term of this patent is extended or adjusted under 35 U.S.C. 154(b) by 225 days.

(21) Appl. No.: 13/002,017

(22) PCT Filed: Jul. 1, 2009

(86) PCT No.: PCT/IB2009/052854
§ 371 (c)(1),
(2), (4) Date: Dec. 29, 2010

(87) PCT Pub. No.: WO2010/001346
PCT Pub. Date: Jan. 7, 2010

(65) Prior Publication Data
US 2011/0109897 A1    May 12, 2011

(30) Foreign Application Priority Data
Jul. 1, 2008  (EP) .................................... 08104597

(51) Int. Cl.
G01N 33/48     (2006.01)
G01N 21/01     (2006.01)
(52) U.S. Cl. .......................................... 356/39; 356/244
(58) Field of Classification Search .............. 356/39–42, 356/244–246
See application file for complete search history.

(56) References Cited

U.S. PATENT DOCUMENTS

| 4,905,169 A | 2/1990 | Buican et al. |
| 7,289,204 B2* | 10/2007 | Nielsen et al. ................. 356/317 |
| 2006/0066867 A1 | 3/2006 | Beausoleil |
| 2007/0030492 A1 | 2/2007 | Novotny et al. |
| 2010/0141938 A1* | 6/2010 | Banerjee et al. .............. 356/246 |

FOREIGN PATENT DOCUMENTS
WO    91/12487 A    8/1991

OTHER PUBLICATIONS

Potyrailo, R., et al. "Optical Waveguide Sensors in Analytical Chemistry; Today's Instrumentation, Applications and Trends for Future Development", Fresenius J. Anal. Chem., vol. 362, pp. 349-373 (1998).

Friis, P., et al. "Monolithic Integration of Microfluidic Channels and Optical Waveguides in Silicon on Silicon," Applied Optics, vol. 40, No. 34, pp. 6246-6251 (Dec. 1, 2001).

(Continued)

Primary Examiner — Michael P Stafira

(57) ABSTRACT

An apparatus comprising at least one measuring cell (10) is disclosed. The measuring cell comprises a first cavity (16 and a second cavity (18) perpendicular to the first cavity, the first cavity and the second cavity comprising an overlap at first respective ends and a reflective surface (20) at the opposite respective ends. A beam splitter (15) is located in the overlap and an electromagnetic radiation source (12) is arranged to project a beam of electromagnetic radiation onto the beam splitter (15) such that the beam is projected into each of the cavities. A phase detector (22) for detecting a phase difference between the respective electromagnetic radiation reflected by the first and second cavity (16; 18) is also provided. In addition, the apparatus has a fluid channel (26), at least a part of which runs parallel to the first cavity (16) such that the electromagnetic radiation projected into the first cavity extends into said part of the fluid channel. This allows for the interferometric detection of particles in the fluid channel.

17 Claims, 2 Drawing Sheets

OTHER PUBLICATIONS

Figure 1:
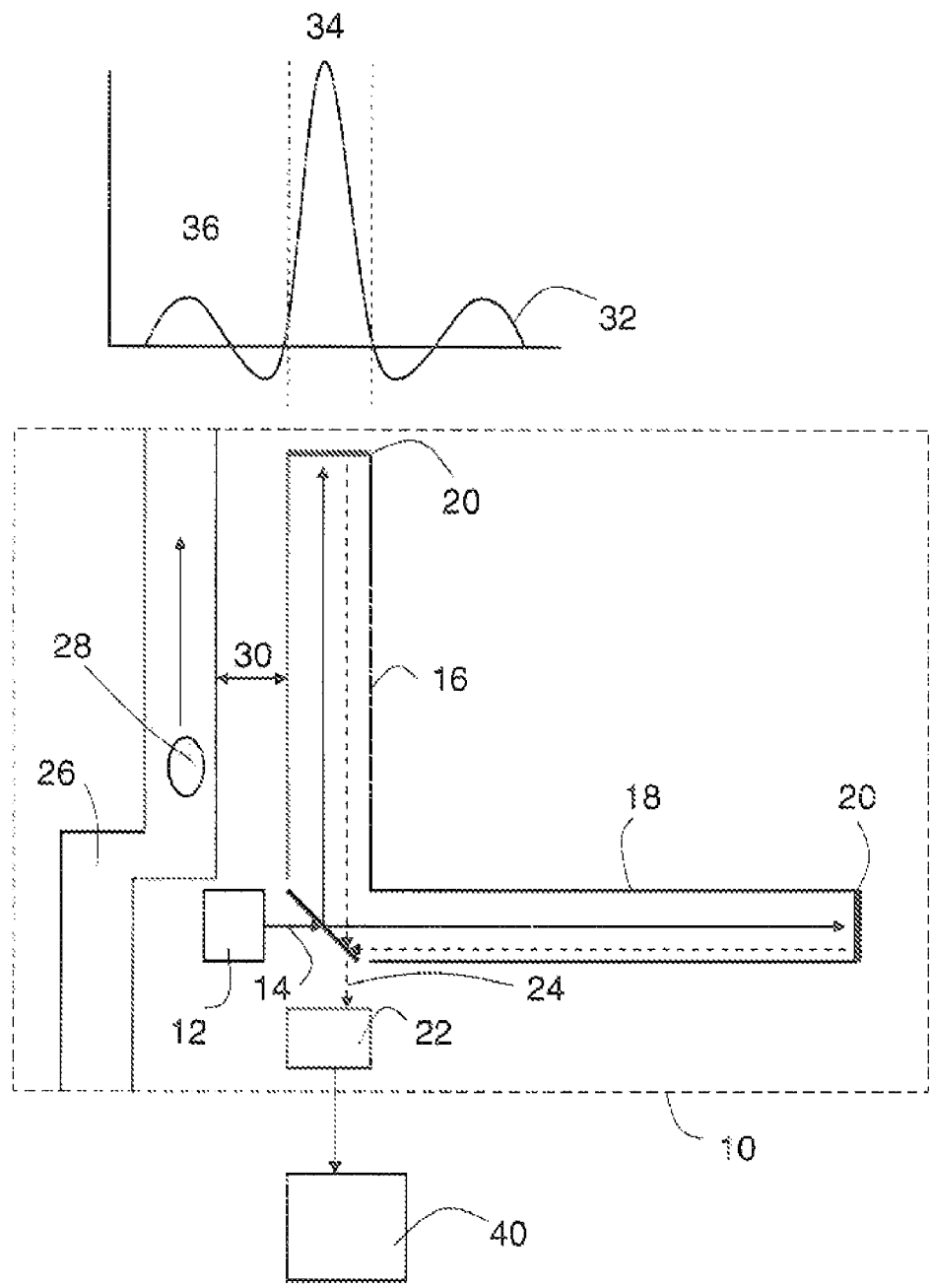

Bernini, R., et al. "ARROW Optical Waveguides Based Sensors," Sensors and Actuators B, Elsevier, vol. 100, Nos. 1-2, pp. 143-146 (2004).

Ymeti, A., et al "Integration of Microfluidics with a Four-Channel Integrated Optical Young Interferometer Immunosensor," Biosensors and Bioelectronics, Elsevier, vol. 20, No. 7, pp. 1417-1421 (2005).

International Search Report and Written Opinion for Int'l. Patent Appln. No. PCT/IB2009/052854 (Nov. 26, 2009).

Dennis, T. et al. "Interferometric Measurement of Refractive-Index Change in Photosensitive Glass," Applied Optics, vol. 40, No. 10, pp. 1663-1667 (Apr. 1, 2001).

* cited by examiner

MEASURING APPARATUS

FIELD OF THE INVENTION

The present invention relates to an apparatus comprising at least one measuring cell, said measuring cell comprising a first cavity, a second cavity perpendicular to the first cavity, the first cavity and the second cavity comprising an overlap at first respective ends, a beam splitter located in the overlap, an electromagnetic radiation source arranged to project a beam of electromagnetic radiation onto the beam splitter and a phase detector for detecting a phase difference between the respective electromagnetic radiation reflected by the first and second cavity.

BACKGROUND OF THE INVENTION

The detection of small particles, e.g. particles having sizes of less than 100 nm, has been drawing considerable interest in recent years. Such particle detection is for instance of interest in the field of nanotechnology, where the detection of the size of such particles can provide relevant information about for instance the particle manufacturing process or about the applicability of the particles for a predetermined purpose. Another application domain where the detection of small particles has become of interest is the medical field, where for instance the detection of e.g. viruses in a fluid such as the human blood can aid the detection of certain diseases in early stages, e.g. prior to the patient demonstrating symptoms indicative of the disease, thus increasing the chance of successful treatment. Other particles that may be detected include polymer molecules, proteins and so on.

In the particle detection field, optical systems are especially attracting interest due to the high resolution of such systems, thereby allowing the detection of very small particles. An example of such a particle detection system is disclosed in US2007/0030492 A1, which uses an interferometric approach by means of detecting the phase difference between a reference beam of electromagnetic radiation and a beam of the same radiation projected through a flow cell. The light scattering caused by the particles in the flow cell causes the reflection of electromagnetic radiation back to a detector, where the phase difference between the backscattered radiation and the reference beam is determined. A drawback of this system is that the particle size resolution is limited to particles having a size of several nanometers. Moreover, the system is relatively large and, as a consequence, relatively costly.

SUMMARY OF THE INVENTION

The present invention seeks to provide an apparatus according to the opening paragraph that overcomes at least some of the problems associated with the prior art arrangements.

According to an aspect of the present invention, there is provided an apparatus comprising at least one measuring cell, said measuring cell comprising a first cavity; a second cavity perpendicular to the first cavity, the first cavity and the second cavity comprising an overlap at first respective ends and a reflective surface at the opposite respective ends; a beam splitter located in the overlap; an electromagnetic radiation source arranged to project a beam of electromagnetic radiation onto the beam splitter; a phase detector for detecting a phase difference between the respective electromagnetic radiation reflected by the first and second cavity; and a fluid channel, at least a part of which runs parallel to the first cavity such that the electromagnetic radiation projected into the first cavity extends into said part of the fluid channel.

Such an apparatus may be advantageously implemented in a silicon device such as an integrated circuit, and has the further advantage that interactions between the fluid in the fluid channel and the electromagnetic beam are extended over the full length of the channel parallel with the first cavity, such that a particle traveling through the channel may be detected in several contiguous measurements, thereby improving the resolution of the detection apparatus because an improved signal to noise ratio (SNR) is obtained. Moreover, because the optical part of the apparatus is not exposed to the fluid, cleaning of the apparatus can be more easily achieved.

Preferably, the part of the fluid channel and the first cavity are separated by a layer of a material having a thickness such that the layer is at least semi-transparent to the electromagnetic radiation. Such materials may be materials that are commonly used in IC manufacturing, such as silicon and silicon oxide.

The detector signal may be processed inside the apparatus. To this end, the apparatus may further comprise a data processing element for processing a detection signal from the detector. The processing element may be arranged to compare the detection signal with at least one predefined signal such that specific types of particles characterized by a specific response signature can be identified.

In an embodiment, the respective reflective surfaces each comprise a Bragg mirror. Such mirrors can be readily formed in an IC manufacturing process, thereby further reducing the complexity of the apparatus of the present invention.

The apparatus may comprise a plurality of said measuring cells. Such a plurality may be used for parallel measurement of multiple samples. To this end, the apparatus may comprise a fluid inlet, wherein the respective fluid channels are coupled in parallel to said fluid inlet. This facilitates the detection of multiple particles at the same time, for instance by the provision of a plurality of data processing elements, each of said elements being coupled to a detector of a respective one of the measuring cells.

Alternatively, the respective fluid channels of said plurality of said measuring cells are connected in series, such that multiple measurements of the same sample may be combined to improve the SNR of the measurement.

In an embodiment, the light source is a laser diode. Such a diode has the advantage that it can be readily integrated into an IC manufacturing process.

BRIEF DESCRIPTION OF THE EMBODIMENTS

Figure 2:
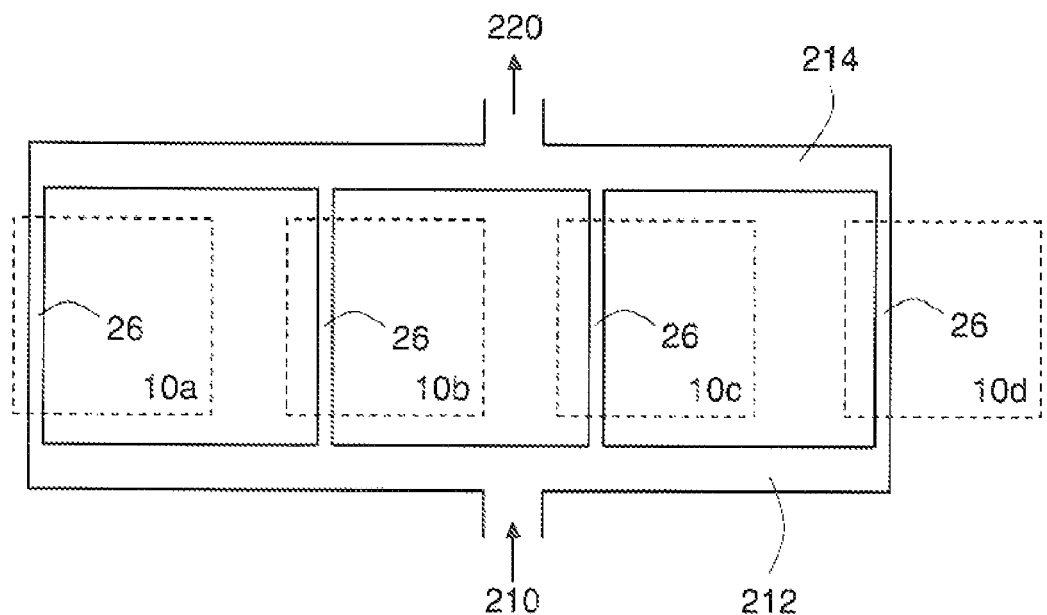
Figure 3:
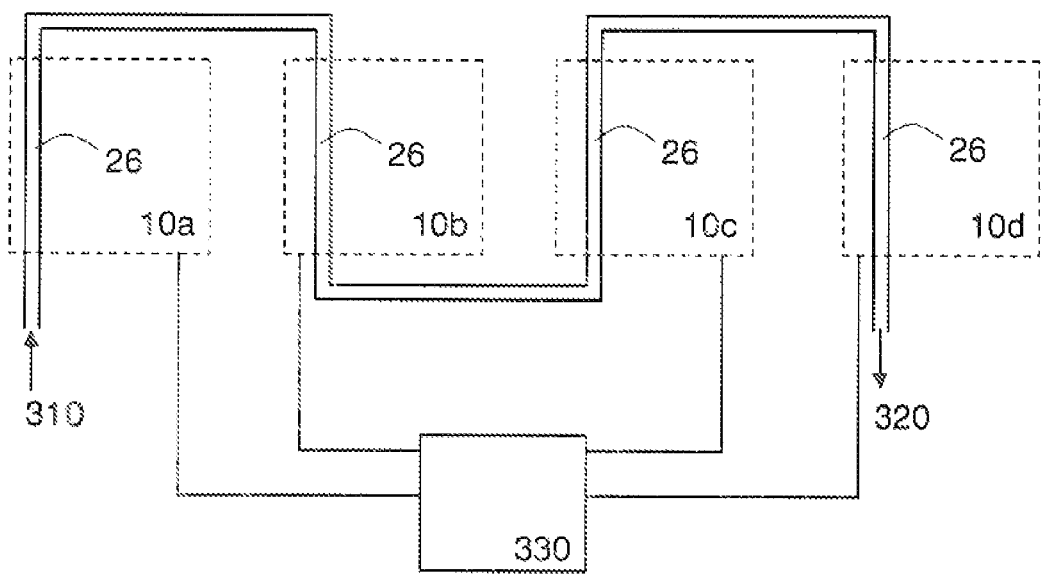

Embodiments of the invention are described in more detail and by way of non-limiting examples with reference to the accompanying drawings, wherein:

FIG. 1 schematically depicts a measuring cell according to an embodiment of the present invention;

FIG. 2 schematically depicts a measuring cell array according to an embodiment of the present invention; and FIG. 3 schematically depicts a measuring cell array according to an alternative embodiment of the present invention.

DETAILED DESCRIPTION OF THE DRAWINGS

It should be understood that the Figures are merely schematic and are not drawn to scale. It should also be understood that the same reference numerals are used throughout the Figures to indicate the same or similar parts.

In FIG. 1, a measuring cell 10 of an apparatus in accordance with an embodiment of the present invention is depicted. The measuring cell 10 preferably is realized in a wafer such as a silicon wafer, a SiGe wafer, a silicon-on-insulator wafer, or any other type of suitable wafer material. The measuring cell 10 comprises a source 12 for generating a beam 14 of electromagnetic radiation, e.g. ultraviolet (UV), visible or infrared (IR) light. For instance, the source 12 may comprise a laser such as a laser diode.

The measuring cell 10 comprises a first cavity 16 and a second cavity 18, each of which have a reflective surface 20 for reflecting the beam 14. The reflective surface may be any suitable mirror. Advantageously, a Bragg mirror is used when the apparatus is realized in silicon because Bragg mirrors can be realized using standard silicon processing steps, e.g. CMOS processing steps. The first cavity 16 and the second cavity 18 may be formed in any suitable way, e.g. by means of an etching or grinding step in case of the apparatus being realized in silicon.

The measuring cell 10 further comprises a beam splitter 15 for splitting the beam 14 such that a portion of the beam is projected into both the first cavity 16 and the second cavity 18. The beam splitter 15 may be realized in any suitable manner, e.g. by the formation of semi-transparent metal layers, e.g. by means of evaporation, or by a pick and place approach in which a semitransparent mirror is direct bonded (e.g. through anodic bonding) to the substrate defining the cavity The beam splitter 15 is further arranged to collect the beams 24 of electromagnetic radiation that are reflected back from the reflective surfaces 20 of the first cavity 16 and the second cavity 18 and to forward these beams to a detector 22.

The detector 22 is arranged to detect a phase difference between the respective beams 24 reflected from the first cavity 16 and the second cavity 18. The operation of such detectors is known from the field of interferometry, and is not discussed in further detail for reasons of brevity only. The interested reader may for instance turn to "Interferometric measurement of refractive-index change in photosensitive glass" by Dennis et al. in Applied Optics, Vol. 40, No. 10 pages 1663-1667 (2001) as well as to US2007/0030492 A1 for a more detailed discussion on this subject. The detector 22 may be any suitable detector, such as split photodetector coupled to a processor 40 for analyzing the phase difference between the respective beams 24. As explained in US2007/0030492 A1, such a detector ensures that the detector 22 is insensitive to noise from the source 12. It will be appreciated that the apparatus of the present invention may comprise further optical components, e.g. a collimating lens, which may be placed in front of the beam splitter 15 in the overlap between the first cavity 16 and the second cavity 18 for collimating a diverging EM beam 14, such as the beam generated by a laser diode. Further non-limiting detector examples include, a Si junction device, a photodiode or a phototransistor. These example detectors can be easily realized in semiconductor manufacturing processes.

The apparatus further comprises a fluid channel 26 at least a part of which runs parallel with the first cavity 16. This parallel part of the fluid channel 26 is separated from the first cavity 16 by a layer of a material 30. The material 30 is at least semi-transparent, i.e. has a relatively small extinction coefficient for the wavelength of the electromagnetic radiation generated by the source 12, such that a part of the beam 14 projected into the first cavity 16 extends into the fluid channel 26. For instance, the material 30 may be silicon or silicon oxide, which are at least semi-transparent to electromagnetic (EM) radiation in the IR band and the visible part of the EM spectrum respectively.

In case of the apparatus being realized in silicon, the fluid channel may be formed in any suitable way, e.g. by means of an etching step followed by an epitaxial silicon growth step to seal the channel, by means of an etching step followed by the deposition of a sacrificial material in the etched trench, coverage of the sacrificial material by a sealing layer and the subsequent removal of the sacrificial material and so on. The formation of buried cavities in a silicon device such as an IC is routine skill for the skilled person.

It will be appreciated that the above described apparatus is an implementation of an interferometer. It will be understood that the specific implementation of this interferometer shown in FIG. 1 is by way of non-limiting example only, and that any suitable type of interferometer may be implemented in this way, e.g. a Michelson interferometer, a Mach-Zender interferometer, a ring resonator and so on.

The present invention is based on the insight that a particle 28 in the fluid channel 26 will cause an interference of the electrical field 32 of the beam 14 running through the first cavity 16. This is because the electrical field 32 has a component 36 that extends into the fluid channel 26 such that the coupling between the component 36 of the electrical field and the particle 28 causes a perturbation of the electrical field 32, thereby altering the phase of the EM wave extending from the cavity into the channel 26 through the (semi-)transparent wall separating the first cavity 16 from the channel 26. This phase change is detected in the main component 34 of the electrical field 32 by the detector 22 by a change in the interference between the reflected beams 24 in between the beam splitter 15 and the detector 22. This interference may be used to identify the particle 28. A particle 28 having a particular size and particular electrical properties (e.g. a particular polarizability) will cause a particular phase change in the beam 14 running through the first cavity 16, which can be used as a signature for this particular particle. To this end, the processor 140 may store a plurality of such signatures and may be arranged to compare the signature retrieved by the detector 22 with the stores signatures to identify the type of particle detected in the fluid channel 26.

It will be appreciated that the width of the first cavity 14 plays an important role in this principle. Typically, the width of the first cavity 14 is chosen such that is about 1 wavelength of the electromagnetic radiation, e.g. around 1 micron wide in case of near-visible IR, such that a substantial part of the wave extends into the material 30 and the fluid channel 26.

In FIG. 1, the apparatus of the present invention comprises a single measurement cell 10 by way of non-limiting example only. In fact, the apparatus of the present invention may comprise many measurement cells 10. An example of a multiple-measurement cell apparatus is shown in FIG. 2. The apparatus comprises a fluid inlet 210 and a fluid outlet 220 for providing four measurement cells 10*a-d* with a sample for measurement. The measurement cells 10*a-d* have been depicted without their interferometer arrangement for reasons of clarity only; it will be understood that each of the measurement cells 10*a-d* comprises such an interferometer arrangement.

The fluid channels 26 of the measurement cells 10*a-d* are coupled in parallel between the fluid inlet 210 and a fluid outlet 220 such that each cell can perform an individual measurement on the sample. This allows for the simultaneous detection of several particles 28. Each measurement cell may be coupled to an individual signal processor (not shown) for processing the signal from the detector 22. Alternatively, two or more measurement cells may share a signal processor.

FIG. 3 shows an alternative embodiment of an apparatus of the present invention having a plurality of measurement cells 10. In this embodiment, the fluid channels 26 of four measurement cells 10a-d are series connected between a fluid inlet 310 and a fluid outlet 320 such that each cell is arranged to detect the same particle 28. A processor 330 is provided to process, e.g. combine, the detection signals from the four measurement cells 10a-d such that an improvement in the SNR is obtained. Typically, a √2 improvement in resolution is obtained for each additional measurement because the random nature of noise implies that the noise characteristics typically scale with a factor √2 whereas the signal characteristics typically scale with a factor 2. Consequently, the accumulation of multiple measurements improves the resolution of the apparatus, thus facilitating the detection of smaller particles. In fact, a sufficient number of measurement cells 10 in series may allow for the detection of (larger size) single molecules such as oligomers or polymers by providing a sufficient improvement of the SNR.

In order to ensure that the processor 330 samples corresponding data signals from the measurement cells 10a-d, a flow meter (not shown) may be placed between the fluid inlet 310 and the fluid outlet 320, with the processor 330 being arranged to determine the point in time for sampling the detection signal of the respective measurement cells based on the flow rate determined by the flow meter.

It will be appreciated that four measurement cells 10a-d in FIGS. 2 and 3 have been shown by way of non-limiting example only. The multi-cell apparatus of the present invention may comprise any number of measurement cells 10, which may be laid out in any suitable fashion, e.g. in the form of a two-dimensional grid.

The apparatus of the present invention may be integrated in an electronic device such as a bed-side patient monitor or a particle size detector, in particular if the apparatus is realized as an IC, because such an IC can be readily integrated in a larger device.

The apparatus of the present invention has the further advantage that the optical components are not in direct contact with the sample fluids provided to the fluid channel(s) 26. This means that the apparatus of the present invention can be readily cleaned after use without the cleaning process being complicated by the exposure of the optical components to the cleaning process.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. An apparatus having at least one measuring cell, said measuring cell comprising:
    a first cavity;
    a second cavity perpendicular to the first cavity, the first cavity and the second cavity having an overlap at first respective ends and a reflective surface at the opposite respective ends;
    a beam splitter located at the overlap;
    an electromagnetic radiation source arranged to project a beam of electromagnetic radiation onto the beam splitter;
    a phase detector for detecting a phase difference between the respective electromagnetic radiation reflected by the first and second cavity; and
    a fluid channel, at least a part of which runs parallel to the first cavity such that the electromagnetic radiation projected into the first cavity extends into said part of the fluid channel.

2. An apparatus according to claim 1, wherein the part of the fluid channel and the first cavity are separated by a layer of a material having a thickness such that the layer is at least semi-transparent to the electromagnetic radiation.

3. An apparatus according to claim 2, wherein the material is silicon.

4. An apparatus according to claim 2, wherein the material is silicon oxide.

5. An apparatus according to claim 1, further comprising a data processing element for processing a detection signal from the phase detector.

6. An apparatus according to claim 5, wherein the processing element is arranged to compare the detection signal with at least one predefined signal.

7. An apparatus according to claim 1, wherein the respective reflective surfaces comprise respective Bragg mirrors.

8. An apparatus according to claim 1, further comprising a plurality of said measuring cells.

9. An apparatus according to claim 8, further comprising a fluid inlet, wherein the respective fluid channels of said measuring cells are coupled in parallel to said fluid inlet.

10. An apparatus according to claim 9, further comprising a plurality of data processing elements, each of said data processing elements being coupled to a detector of a respective one of the measuring cells.

11. An apparatus according to claim 8, wherein the respective fluid channels of said plurality of said measuring cells are connected in series.

12. An apparatus according to claim 1, wherein the light source is a laser diode.

13. An apparatus according to claim 1, wherein the at least one measuring cell is part of an integrated circuit.

14. An electronic device comprising an integrated circuit according to claim 13.

15. An electronic device according to claim 14, wherein the integrated circuit is configured to receive a human blood sample.

16. An electronic device according to claim 14, wherein the integrated circuit is configured to receive a fluid and is configured for detection of viruses in the fluid.

17. An electronic device according to claim 16, wherein the integrated circuit is configured to receive a human blood sample.

* * * * *